US012102710B2

(12) United States Patent
Hitchcock et al.

(10) Patent No.: US 12,102,710 B2
(45) Date of Patent: Oct. 1, 2024

(54) PROBIOTIC SKIN FORMULATIONS (71) Applicant: CROWN LABORATORIES, INC., Johnston City, TN (US)

(72) Inventors: Thomas M. Hitchcock, Dallas, TX (US); Sasima Phadungpojna, Bristol, TN (US); Matthew D. Stephens, Kingsport, TN (US); Mun Su Rhee, Johnson City, TN (US)

(73) Assignee: CROWN LABORATORIES, INC., Johnson City, TN (US)

( * ) Notice: Subject to any disclaimer, the term of this patent is extended or adjusted under 35 U.S.C. 154(b) by 20 days.

(21) Appl. No.: 17/353,956

(22) Filed: Jun. 22, 2021

(65) Prior Publication Data

US 2021/0393510 A1 Dec. 23, 2021

Related U.S. Application Data (60) Provisional application No. 63/042,684, filed on Jun. 23, 2020.

(51) Int. Cl.
| | |
|---|---|
| *A61K 8/99* | (2017.01) |
| *A61K 8/02* | (2006.01) |
| *A61K 8/04* | (2006.01) |
| *A61K 8/19* | (2006.01) |
| *A61K 8/34* | (2006.01) |
| *A61K 8/37* | (2006.01) |
| *A61K 8/67* | (2006.01) |
| *A61K 8/73* | (2006.01) |
| *A61K 8/88* | (2006.01) |
| *A61K 8/92* | (2006.01) |
| *A61K 8/9789* | (2017.01) |
| *A61K 9/06* | (2006.01) |
| *A61K 9/19* | (2006.01) |
| *A61K 31/07* | (2006.01) |
| *A61K 35/741* | (2015.01) |
| *A61K 47/14* | (2017.01) |
| *A61K 47/34* | (2017.01) |
| *A61K 47/44* | (2017.01) |
| *A61K 47/46* | (2006.01) |
| *A61Q 19/00* | (2006.01) |

(52) U.S. Cl.
CPC ............... *A61K 8/99* (2013.01); *A61K 8/022* (2013.01); *A61K 8/042* (2013.01); *A61K 8/19* (2013.01); *A61K 8/34* (2013.01); *A61K 8/37* (2013.01); *A61K 8/671* (2013.01); *A61K 8/735* (2013.01); *A61K 8/88* (2013.01); *A61K 8/922* (2013.01); *A61K 8/9789* (2017.08); *A61K 9/06* (2013.01); *A61K 9/19* (2013.01); *A61K 31/07* (2013.01); *A61K 35/741* (2013.01); *A61K 47/14* (2013.01); *A61K 47/34* (2013.01); *A61K 47/44* (2013.01); *A61K 47/46* (2013.01); *A61Q 19/00* (2013.01); *A61K 2800/524* (2013.01); *A61K 2800/594* (2013.01)

(58) Field of Classification Search
CPC .......... A61K 8/99; A61K 8/022; A61K 8/042; A61K 8/19; A61K 8/34; A61K 8/37; A61K 8/671; A61K 8/735; A61K 8/88; A61K 8/922; A61K 8/9789; A61K 9/06; A61K 9/19; A61K 31/07; A61K 35/741; A61K 47/14; A61K 47/34; A61K 47/44; A61K 47/46; A61K 2800/524; A61K 2800/594; A61K 2800/31; A61K 9/0014; A61K 47/32; A61Q 19/00; A61P 1/00
See application file for complete search history.

(56) References Cited

U.S. PATENT DOCUMENTS

| | | | |
|---|---|---|---|
| 4,663,306 A | 5/1987 | Cantrell | |
| 5,837,509 A | 11/1998 | Israelsen et al. | |
| 7,179,458 B2 | 2/2007 | Chang et al. | |
| 7,427,397 B2 * | 9/2008 | Adams | A23L 29/065 |
| | | | 424/93.4 |
| 8,481,299 B2 | 7/2013 | Gueniche | |
| 8,496,917 B2 | 7/2013 | Chaudhuri | |
| 8,557,249 B2 | 10/2013 | Brooks et al. | |
| 9,636,292 B2 | 5/2017 | Sweeney et al. | |
| 9,713,596 B2 | 7/2017 | Hong et al. | |
| 9,889,165 B2 * | 2/2018 | Taylor | A61P 43/00 |

(Continued)

FOREIGN PATENT DOCUMENTS

| | | | |
|---|---|---|---|
| CN | 100490941 C | * | 5/2009 |
| EP | 0965641 A2 | | 12/1999 |

(Continued)

OTHER PUBLICATIONS

Lennox (Maintenance of Bacterial Cultures on Anhydrous Silica Gel, The American Biology Teacher, Mar. 1, 1977 39(3): 152-154) can be found at this webpage (https://online.ucpress.edu/abt/article-abstract/39/3/152/11424/Maintenance-of-Bacterial-Cultures-on-Anhydrous?redirectedFrom=fulltext) (Year: 1977).*
Derm Collective (https://dermcollective.com/retinyl-palmitate/#:~:text=Retinyl%20palmitate%E2%80%94also%20known%20as,benefits%20by%20boosting%20collagen%20production.) Nov. 25, 2019 (Year: 2019).*
Making Cosmetics® (chrome-extension://efaidnbmnnnibpcajpcglclefindmkaj/https://www.makingcosmetics.us/fact-sheets/fact-sheet-polyamide-3.pdf) Nov. 2, 2018 (Year: 2018).*

(Continued)

*Primary Examiner* — Aaron J Kosar
*Assistant Examiner* — Jacob A Boeckelman
(74) *Attorney, Agent, or Firm* — Michael Best & Friedrich LLP (57) ABSTRACT

Described herein are dermatological compositions, formulations containing wild type or genetically modified *Cutibacterium* bacteria and methods for use thereof of skin. The cosmetic and therapeutic formulations described herein can be used as cosmetic daily skin treatments or for treating skin inflammation or disorders including acne, psoriasis, rosacea, dermatitis, or eczema.

2 Claims, 3 Drawing Sheets

(56) References Cited

U.S. PATENT DOCUMENTS

| | | | |
|---|---|---|---|
| 10,201,509 B2 | 2/2019 | Garcines et al. | |
| 10,434,073 B2 | 10/2019 | Tong et al. | |
| 10,471,035 B2 | 11/2019 | Bojanowski | |
| 10,568,819 B2 | 2/2020 | Chaudhuri | |
| 10,584,344 B2 | 3/2020 | Hitchcock et al. | |
| 10,597,402 B2 | 3/2020 | Chaudhuri | |
| 10,660,831 B2 | 5/2020 | Albrecht | |
| 2002/0090678 A1 | 7/2002 | Kordyum et al. | |
| 2003/0175274 A1 | 9/2003 | Rosen et al. | |
| 2003/0199440 A1 | 10/2003 | Dack et al. | |
| 2006/0183188 A1 | 8/2006 | Pel et al. | |
| 2008/0207515 A1 | 8/2008 | Ferguson et al. | |
| 2008/0248477 A1 | 10/2008 | Holtzman et al. | |
| 2009/0022700 A1 | 1/2009 | Cassin et al. | |
| 2009/0232785 A1 | 9/2009 | Breton et al. | |
| 2010/0047394 A1 | 2/2010 | May | |
| 2011/0027221 A1 | 2/2011 | Fu et al. | |
| 2012/0301452 A1 | 11/2012 | Gueniche et al. | |
| 2013/0108584 A1 | 5/2013 | Jan et al. | |
| 2013/0266539 A1* | 10/2013 | Borody | A61K 9/19 424/93.3 |
| 2014/0023618 A1 | 1/2014 | Goren et al. | |
| 2014/0044653 A1* | 2/2014 | Qvit-Raz | A61Q 17/04 424/59 |
| 2014/0044677 A1 | 2/2014 | Qvit-Raz et al. | |
| 2014/0065209 A1 | 3/2014 | Putaala et al. | |
| 2014/0072583 A1 | 3/2014 | Ardeleanu et al. | |
| 2015/0071957 A1 | 3/2015 | Kelly et al. | |
| 2015/0086581 A1 | 3/2015 | Li et al. | |
| 2015/0361436 A1* | 12/2015 | Hitchcock | C07K 14/715 424/93.2 |
| 2016/0200789 A1 | 7/2016 | Hemmerle et al. | |
| 2016/0264998 A1 | 9/2016 | Kim et al. | |
| 2016/0271257 A1 | 9/2016 | Bredehorst et al. | |
| 2017/0065647 A1 | 3/2017 | Kim et al. | |
| 2017/0304373 A1 | 10/2017 | Taylor et al. | |
| 2019/0060374 A1* | 2/2019 | Hitchcock | C07K 14/485 |
| 2019/0336542 A1* | 11/2019 | Taylor | A61P 17/06 |

FOREIGN PATENT DOCUMENTS

| | | | |
|---|---|---|---|
| EP | 1110555 A1 | 6/2001 | |
| EP | 2364712 A1 | 9/2011 | |
| KR | 20090098419 A | 9/2009 | |
| WO | WO9967356 A | 12/1999 | |
| WO | WO2001081581 A2 | 11/2001 | |
| WO | WO2003033515 A1 | 4/2003 | |
| WO | WO2006058243 A2 | 6/2006 | |
| WO | WO2010013179 A1 | 2/2010 | |
| WO | WO2010061226 A1 | 6/2010 | |
| WO | WO2011060488 A1 | 5/2011 | |
| WO | WO2013122931 A2 | 8/2013 | |
| WO | WO2013142378 A1 | 9/2013 | |
| WO | WO2014025938 A1 | 2/2014 | |
| WO | 2015195845 A1 | 12/2015 | |
| WO | 2017044835 A1 | 3/2017 | |
| WO | 2017147507 A1 | 8/2017 | |
| WO | 2020099663 A1 | 5/2020 | |

OTHER PUBLICATIONS

Cosmetics and Toiletries (https://www.cosmeticsandtoiletries.com/cosmetic-ingredients/actives/news/21843120/sensolene-light-awarded-for-2019-best-new-ingredient) Jan. 17, 2020. (Year: 2020).*

CN100490941C claims translated, 1 page (Year: 2009).*

CN100490941C description translated, 4 pages (Year: 2009).*

Louwen et al., "The Role of CRISPR-Cas Systems in Virulence of Pathogenic Bacteria", Microbiology and Molecular Biology Reviews, 2015, vol. 78, No. 1, pp. 74-78.

Karlyshev et al., "Development and Application of an Insertional System for Gene Delivery and Expression in Campylobacter jejuni", Applied and Environmental Microbiology, 2005, vol. 71, No. 7, pp. 4004-4013.

Linares et al., "An agmatine-inducible system for the expression of recombinant proteins in Enterococcus faecalis", Microbial Cell Factories, 2014, vol. 13, No. 169, 9 pages.

Husseiny et al., "Rapid Method for the Construction of *Salmonella enterica* Serovar Typhimurium Vaccine Carrier Strains", Infection and Immunity, 2005, vol. 73, No. 3, pp. 1598-1605.

Al-Mamun et al., "Characterization and evaluation of antibacterial and antiproliferative activities of crude protein extracts isolated from the seed of Ricinus communis in Bangladesh", BMC Comp. Alt. Med., vol. 16, No. 211, 2016, pp. 1-10.

Momoh et al., "Evaluation of the antimicrobial and phytochemical properties of oil from castor seeds (*Ricinus communis* linn)", Bul. Environ. Pharm. Life Science, vol. 1, 2012, pp. 21-27.

Rampadarath et al., "In vitro antimicrobial and larvicidal properties of wild *Ricinus communis* L. in Mauritius", Asian Pac. J. Trop. Biomedicine, vol. 6, No. 2, 2016, pp. 100-107.

International Search Report for Application No. PCT/US2017/019476 dated Jun. 8, 2017 (13 pages).

International Search Report and Written Opinion for Application No. PCT/US2015/0363306 dated Sep. 17, 2015 (12 pages).

Allhorn et al., "A novel enzyme with antioxidant capacity produced by the ubiquitous skin colonizer Propionibacterium acnes", Scientific Reports, 2016, pp. 1-12.

Asadullah et al., "IL-10 is a Key Cytokine in Psoriasis. Proof of Principle by IL-10 Therapy: A New Therapeutic Approach", J. Clinical Investigation, 1998, vol. 101, No. 4, pp. 783-794.

Aubin et al., "Propionibacterium acnes, an emerging pathogen: From acne to implant-infections, from phylotype to resistance", Science Direct, 2014, pp. 241-250.

Beylot et al., "Propionibacterium acnes: an update on its role in the pathogenesis of acne", JEADV, 2014, vol. 28, pp. 271-278.

Biswas et al., "High-efficiency gene inactivation and replacement system for gram-positive bacteria," J Bacteriol, 1993, 175(11): 3628-3635.

Blinkovsky et al., "Purification characterization, and Heterologious Expression in Fusarium venatum of a Novel Serine Carboxypeptidase from Aspergillus oryzae", Applied and Environmental Microbiology, 1999, vol. 65, No. 8, pp. 3298-3303.

Bowe et al., "Acne vulgaris, probiotics and the gut-brain-skin-axis—back to the future?", Gut Pathogens, 2011, vol. 3, No. 1, pp. 1-11.

Brautaset et al., "Positively Regulated bacterial expression systems", Microbiol. Biotechnology, 2009, vol. 2, No. 1, pp. 15-30.

Bruggemann et al., "CriSPR/cas loci of type II Propionibacterium acnes confer immunity against acquisition of mobile elements present in type IP. Acnes", PLoS One, vol. 7, No. 3, 2012, pp. 1-10.

Bruggemann, "Insights in the Pathogenic Potential of Propionibacterium acnes from its Complete Genome", Semin. Cutan. Med. Surg., 2005, vol. 24, pp. 67-72.

Cheong et al., "Optimization of electrotransformation conditions for Propionibacterium acnes", Journal of Microbiol. Methods, 2008, vol. 72, No. 1, pp. 38-41.

Database GenBank: AAP15998, Sep. 29, 1999, 1 page.

Database GenBank: AAP61879, Jun. 12, 2003, 1 page.

Database GenBank: AAP61880, Jun. 12, 2003, 1 page.

Database GenBank: AJN04212, Feb. 13, 2015, 1 page.

De Vries et al., "Integration of foreign DNA during natural transformation of *Acinetobacter* sp. by homology-facilitated illegitimate recombination,", PNAS, 2002, 99(4): 2094-2099.

Falentin et al., "The Complete Genome of Propionibacterium freudenreichii CIRM-BIA1T, a Hardy Actinobacterium with Food and Probiotic Applications", PLoS One, 2010, vol. 5, No. 7, e11748, 12 pages.

Fitz-Gibbon et al., "Propionibacterium acnes strain populations in the human skin microbiome associated with acne", J. Invest. Dermatol., 2013, vol. 133, No. 9, pp. 2152-2160.

Haubner et al., "Wound healing after radiation therapy: Review of the literature", Radiation Oncology, 2012, vol. 7, No. 162, 9 pages.

Holland et al., "Proteomic identificaiton of secreted proteins of Propionibacterium acnes", BMC Microbiol., 2010, vol. 10, No. 230, 11 pages.

Horvath et al., "CRISPR/Cas, the Immune System of Bacteria and Archaea", Science, 2010, vol. 327, pp. 167-170.

(56) References Cited

OTHER PUBLICATIONS

Husson et al., "Gene replacement and expression of foreign DNA in mycobacteria," J Bacteriol, 1990, 172(2): 519-524.
Jakab et al., "Severe Infections Caused by Propionibacterium acnes: An Underestimated Pathogen in Late Postoperative Infections", Yale Journal of Biology and Medicine, 1996, vol. 69, pp. 477-482.
Jonczyk-Matysiak et al., "Prospects of Phage Appplication in the Treatment of Acne Caused by Propionibacterium acnes", Frontiers in Microbiology, 2017, vol. 8, No. 164, pp. 1-11.
Jore et al., "Efficient Transformation System Propionibacterium freudenreichii based on a novel vector", Society, 2001, vol. 67, No. 2, pp. 499-503.
Kim et al., "Activiation of Toll-Like Receptor 2 in Acne Triggers Inflammatory Cytokine Responses", The Journal of Immunology, 2002, vol. 169, pp. 1535-1541.
Kobayashi et al., "Essential Bacillus subtilis genes", PNAS, 2003, vol. 100, No. 8, pp. 4678-4683.
Le Breton et al., "Genetic Manipulation of *Streptococcus pyogenes* (The Group A *Streptococcus*, GAS)", Curr. Protoc. Microbiol., 2018, vol. 30, 33 pages.
Liu et al., "The diversity and host interactions of Propionibacterium acnes bacteriophages on human skin," The ISME Journal, 2015, 9: 2078-2093.
LSTM Liverpool School of Tropical Medicine, <http://www.lstmliverpool.ac.uk/about-lstm/news-and-media/latest-news/topical-probiotics-new-approaches>, accesssed 2014, 1 page.
Makarova et al., "Ecolution and classification of the CRISPR-Cas systems", Nat. Rev. Microbiol., 2011, vol. 9, No. 4, pp. 67-77.
McDowell et al., "The Opportunisitic Pathogen Propionibacterium acnes: Insights into Typing, Human Disease, Clonal Diversification and CAMP Factor Evolution", PLoS One, 2013, vol. 8, No. 9, e70897.
McShan et al., "Genome Sequence of a Nephritogenic and Highly Transformable M49 Strain of *Streptococcus pyogenes*", J. Bacteriology, 2008, pp. 7773-7785.
Mierau et al., "10 Years of the nisin-controlled gene expression system (NICE) in Lactococcus lactics", Appl. Micriobiol. Biotechnol., 2005, pp. 1-13.
Munikumar et al., "In Silico Identification of Common Putative Drug Targets among the Pathogens of Bacterial Meningitis", Biochem. Anal. Biochem., 2012, vol. 1, No. 123, pp. 1-8.
Nakatsuji et al., "Dermatological Therapy by Topical Application of Non-Pathogenic Bacteria", Journal of Investigative Dermatology, 2014, vol. 134, pp. 11-14.
Ouwehand et al., "Probiotics for the skin: a new area of potential application?", Letters in Applied Microbiology, 2003, vol. 36, pp. 327-331.
Ouwehand et al., "The Potential of Probiotics and Prebiotics for Skin Health", Textbook of Aging Skin, 2010, pp. 799-809.
Parizzi et al., "Te genome sequence of Propionibacterium acidipropionici provides insights into its biotechnological and industrial potential", BMC Genomics, 2012, vol. 13, 20 pages.
Portillo et al., "Propionibacterium acnes: An Underestimated Pathogen in Implant-Associated Infections", BioMed Research International, 2013, pp. 1-11.
Probiotic Action, <https://probioticaction.com>, accessed Apr. 2016, 2 pages.
Pyne et al., "Harnessing heterologous and endogenous CRISPR-Cas machineries for efficient markerless genome editing in Clostridum", Scientific Reports, 2016, pp. 1-15.
Rhee et al., "Development of plasmid vector and electroporation condition for gene transfer in sporogenic lactic acid bacterium, Bacillus coagulans", Plasmid, 2007, vol. 58, No. 1, pp. 13-22.
Rovner et al., "Recoded organisms engineered to depend on synthetic amino acids", Nature, 2015, vol. 518, pp. 89-93. 18 pages.
Sanders et al., "Selected topics in probiotics and prebiotics: meeting report for the 2004 international scientific association for probiotics and prebiotics", Curr. Issues Intest. Microbiol., 2015, vol. 6, No. 2, pp. 55-68.
Sorenson et al., "Mutagenesis of Propionibacterium acnes and analysis of two CAMP factor knock-out mutants", J. Microbiol. Methods, 2010, 23 pages.
Tsai et al., "Rosmarinus officinalis Extract Suppresses Propionibacterium acnes-Induced Inflammatory Responses", J. Med. Food, 2013, vol. 16, No. 4, pp. 324-333.
Vyas et al., "Carrier-Based Drug Delivery System for Treatment of Acne", The Scientific World Journal, 2014, 14 pages.
Wang et al., "A Precision Microbiome Approach Using Sucrose for Selective Augmentation of *Staphylococcus epidermidis* Fermentation against Propionibacterium acnes", Int. J. Mal. Sci., 2016, vol. 17, No. 1870, pp. 1-12.
Xiao et al., "Structure Basis for Directional R-loop Formation and Substrate Handover Mechanisms in Type I CRISPR-Cas System", Cell, 2017, vol. 170, pp. 48-60.
Yan-bin et al., "A review on immune system of the bacteria and its s versus non-self discrimination", Chinese Veterinary Science, 2012, vol. 42, No. 6, pp. 657-660.
Canadian Office Action for Application No. 2950945, dated Feb. 27, 2023 (3 pages).
European Patent Office Action for Application No. 15809700.6 dated May 10, 2023 (5 pages).
European Patent Office. Office Action for Application No. 15809700.6, dated Apr. 19, 2024 (4 pages).
Chinese Patent Office Action for Application No. 201580031622.3 dated Apr. 1, 2024 (40 pages including English translation).
International Search Report and Written Opinion for Application No. PCT/US21/38333 dated Sep. 24, 2021 (11 pages).

* cited by examiner

PROBIOTIC SKIN FORMULATIONS

CROSS-REFERENCE TO RELATED APPLICATIONS

This application claims priority to U.S. Provisional Patent Application No. 63/042,684, filed on Jun. 23, 2020, which is incorporated by reference herein.

TECHNICAL FIELD

Described herein are dermatological compositions, formulations containing wild type or genetically modified *Cutibacterium* bacteria and methods for use thereof of skin. The cosmetic and therapeutic formulations described herein can be used as cosmetic daily skin treatments or for treating skin inflammation or disorders including acne, psoriasis, rosacea, dermatitis, or eczema.

BACKGROUND

The microbiome is a complex network of micro-organisms that live in and on the human body. On the skin, there are billions of microbes consisting of bacteria, viruses, fungi, and archaea. These microbes can be either commensal (helpful), pathogenic (harmful), or symbiotic. Symbiosis occurs when the skin's microbes depend on the human host just as much as the host depends on the microbes. When this relationship is out of balance, it can lead to issues such as opportunistic infections, inflammatory diseases, or accelerated aging. This is known as dysbiosis.

In particular, human skin contains a variety of symbiotic microorganisms that are necessary for healthy skin. These commensal or mutualistic bacteria live in the epidermis and the upper regions of hair follicles. These microorganisms prevent infections from transient pathogenic organisms by competing for nutrients, the production of antibacterial compounds, or by stimulating the skin's immune system. While most skin flora are commensal, some particular bacteria can cause non-infectious skin diseases such as acne, psoriasis, rosacea, dermatitis, or eczema. For example, acne vulgaris is associated with high populations of certain strains of *Cutibacterium acnes*. This causes excess sebum production and skin inflammation commonly observed in acne. The typical treatment is topical and systemic antibiotics which not only kill the pernicious *Cutibacterium* acne organisms, but also kill the other commensal bacteria.

Traditionally, skincare regimens have focused heavily on the interaction of ingredients with human skin cells, while unknowingly disrupting the skin microbiota through ingredients such as antimicrobials and harsh preservatives. Studies now show that microbes living in and on skin secrete beneficial substances that directly impact and are critical to skin health. Therefore, it is important to facilitate the growth of symbiotic microbes on skin.

Skincare products containing harsh ingredients can disrupt the microbiota and lead to dysbiosis, which includes an imbalance in the number of "helpful" and "harmful" microbes (and the molecules they secrete).

What is needed are dermatological compositions containing probiotic components and dormant genetically modified organisms that can ameliorate the harmful effects of pathogenic bacteria while augmenting the skin's natural microbiome.

SUMMARY

One embodiment described herein is an anhydrous dermatological composition comprising: about 0.1% to about 5% by mass of one or more wild type or growth-arrested genetically modified bacteria or probiotic components; and about 95% to about 99.9% by mass of one or more dermatologically acceptable anhydrous excipients. In one aspect, the dermatologically acceptable anhydrous excipients comprise one or more emollients, humectants, moisturizers, vitamins, vitamin analogues, gelling agents, rheology modifiers, pH modifiers, or preservatives; and optionally, one or more solvents.

Another embodiment described herein is an anhydrous dermatological composition comprising: one or more growth-arrested genetically modified microorganisms; and one or more dermatologically acceptable anhydrous excipients comprising one or more emollients, humectants, vitamins, vitamin analogues, or gelling agents. In one aspect, the anhydrous dermatological composition maintains the growth-arrested genetically modified microorganisms in a dormant state for at least six months and up to about 2 years.

Another embodiment described herein is an anhydrous dermatological composition comprising: about 0.1% to about 5% by mass of a growth-arrested strain of *C. acnes*; and about 95% to about 99.9% by mass of one or more dermatologically acceptable anhydrous excipients comprising one or more emollients, humectants, vitamins, vitamin analogues, or gelling agents. In one aspect, the anhydrous dermatological composition maintains the growth-arrested strain of *C. acnes* in a dormant state for at least six months and up to about 2 years. In another aspect, the composition comprises: about 1% to 2% by mass of the growth-arrested strain of *C. acnes*; about 90% by mass of one or more emollients; and about 10% by mass of one or more gelling agents. In another aspect, the growth-arrested strain of *C. acnes* comprises a lyophilized powder comprising *C. acnes*, sodium chloride, calcium stearate, and inulin (fructose polysaccharide). In another aspect, the emollients comprise ethyl olivate, *Olea europaea* leaf extract, and castor oil; and the gelling agent comprises Polyamide-3 (dilinoleic acid, ethylenediamine, polypropylene glycol diamine end-capped with PEG/PPG-32/10 aminopropyl methyl ether). In another aspect, the composition comprises: about 0.1-5% by mass of the growth-arrested strain of *C. acnes*; about 55-95% by mass of ethyl olivate and *Olea europaea* leaf extract; about 20-40% by mass of castor oil; and about 1-15% by mass of Polyamide-3 (dilinoleic acid, ethylenediamine, polypropylene glycol diamine end-capped with PEG/PPG-32/10 aminopropyl methyl ether). In another aspect, the composition comprises: about 1% to 2% by mass of a growth-arrested strain of *C. acnes*; about 1% by mass of Vitamin A or a vitamin A analogue; about 90% by mass of one or more emollients; and about 10% by mass of one or more gelling agents. In another aspect, the composition comprises: about 0.1-5% by mass of the growth-arrested strain of *C. acnes*; about 0.1-5% by mass of retinol; about 0.1-5% by mass of Vitamin A palmitate; about 50-75% by mass of ethyl olivate and *Olea europaea* leaf extract; about 20-40% by mass of castor oil; and about 1-15% by mass of Polyamide-3 (dilinoleic acid, ethylenediamine, polypropylene glycol diamine end-capped with PEG/PPG-32/10 aminopropyl methyl ether).

Another embodiment described herein is an aqueous dermatological composition comprising: about 0.1% to about 5% by mass of probiotic composition; and about 95% to about 99.9% by mass of one or more dermatologically acceptable excipients comprising one or more humectants, moisturizers, rheology modifiers, pH modifiers, preservatives, or solvents. In one aspect, the probiotic composition comprises a *C. acnes* fermentation product comprising lyophilized powder of purified *C. acnes* roxP fermentation media. In another aspect, the *C. acnes* fermentation product is purified using filtration and diafiltration. In another aspect, the composition comprises: about 0.1% to 5% by mass of the *C. acnes* fermentation product; about 80% by mass of one or more solvents; about 10% by mass of one or more humectants; about 1% by mass of one or more moisturizers; about 2% by mass of one or more rheology modifiers; about 4% by mass of one or more film formers; about 2% by mass of one or more preservatives; and about 1% by mass of one or more pH modifiers. In another aspect, the composition comprises: about 0.1-5% by mass of the *C. acnes* fermentation product; about 70-90% by mass of water; about 0.1-5% by mass of sodium hyaluronate solution; about 5-15% by mass of acetamidoethoxyethanol; about 1-5% by mass of polyurethane; about 0.1-5% by mass of a solution of sodium protocatechuic acid, sodium lactate, protocatechuic acid, arginine, aspartic acid, glycine, alanine, serine, valine, proline, threonine, isoleucine, histidine, and phenylalanine (Prodew® 500); about 0.1-5% by mass of hydroxyethyl acrylate, sodium acryloyldimethyl taurate copolymer; about 0.1-5% by mass of polyacrylate crosspolymer-6; about 0.1-5% by mass of benzyl alcohol; about 0.5-1.5% by mass of sodium benzoate and potassium sorbate; and about 0.1-5% by mass of citric acid solution (50%). In another aspect, the composition further comprises about 0.1% to about 2% by mass retinoid.

Another embodiment described herein is a method for preparing a probiotic fermentation product, the method comprising: growing a microorganism in a fermentation medium; separating the fermentation medium from the microorganism; performing tangential flow filtration on the fermentation media with buffer exchanges to remove small molecule contaminants to produce a purified fermentation product; and lyophilizing the purified fermentation product. In one aspect, the microorganism is *C. acnes* roxP.

Another embodiment described herein is a fermentation product produced by any of the methods or means described herein.

Another embodiment described herein is a method for augmenting the skin microbiome, the method comprising administering an effective amount of a dermatological composition comprising: about 0.1% to about 5% by mass of one or more growth-arrested genetically modified bacteria or probiotic components; and about 95% to about 99.9% by mass of one or more dermatologically acceptable excipients.

Another embodiment described herein is a method to minimize pathogenic bacterial growth on the skin, the method comprising: applying to skin an effective amount of a dermatological composition comprising: about 0.1% to about 5% by mass of one or more growth-arrested genetically modified bacteria or probiotic components; and about 95% to about 99.9% by mass of one or more dermatologically acceptable excipients.

Another embodiment described herein is a method of treating acne, the method comprising applying to skin an effective amount of a dermatological composition comprising: about 0.1% to about 5% by mass of one or more growth-arrested genetically modified bacteria or probiotic components; and about 95% to about 99.9% by mass of one or more dermatologically acceptable excipients.

Another embodiment described herein is a method for preparing a cosmetic or therapeutic composition comprising combining: about 0.1% to about 5% by mass of one or more growth-arrested genetically modified bacteria or probiotic components; and about 95% to about 99.9% by mass of one or more dermatologically acceptable excipients.

Another embodiment described herein is a cosmetic or therapeutic composition prepared by any of the methods or means described herein.

Another embodiment described herein is a means for preparing a cosmetic or therapeutic composition comprising combining: about 0.1% to about 5% by mass of one or more growth-arrested genetically modified bacteria or probiotic components; and about 95% to about 99.9% by mass of one or more dermatologically acceptable excipients.

Another embodiment described herein is the use of a cosmetic or therapeutic composition comprising one or more growth-arrested genetically modified bacteria or probiotic components; and about 95% to about 99.9% by mass of one or more dermatologically acceptable excipients for the treatment of dermatological diseases or disorders.

DETAILED DESCRIPTION

Unless otherwise defined, all technical and scientific terms used herein have the same meaning as commonly understood by one of ordinary skill in the art. For example, any nomenclatures used in connection with, and techniques of, cell and tissue culture, molecular biology, immunology, microbiology, genetics, and protein and nucleic acid chemistry and hybridization described herein are well known and commonly used in the art. In case of conflict, the present disclosure, including definitions, will control. Exemplary methods and materials are described below, although methods and materials similar or equivalent to those described herein can be used in practice or testing of the embodiments and aspects described herein.

As used herein, the term "Xycrobe" or "Xycrobes" refer to a genetically modified strain of *Cutibacterium acnes*, also known as *Propionibacterium acnes*, that has been growth arrested. This strain is described in U.S. Pat. No. 10,584,344 B2 and International Patent Application Publication No. WO 2015195845 A, both of which are incorporated by reference herein for such teachings.

As used herein, the terms "amino acid," "nucleotide," "polynucleotide," "vector," "polypeptide," and "protein"

have their common meanings as would be understood by a biochemist of ordinary skill in the art. Standard single letter nucleotides (A, C, G, T, U) and standard single letter amino acids (A, C, D, E, F, G, H, I, K, L, M, N, P, Q, R, S, T, V, W, or Y) are used herein.

As used herein, the terms such as "include," "including," "contain," "containing," "having," and the like mean "comprising." The present disclosure also contemplates other embodiments "comprising," "consisting of," and "consisting essentially of," the embodiments or elements presented herein, whether explicitly set forth or not.

As used herein, the term "a," "an," "the" and similar terms used in the context of the disclosure (especially in the context of the claims) are to be construed to cover both the singular and plural unless otherwise indicated herein or clearly contradicted by the context. In addition, "a," "an," or "the" means "one or more" unless otherwise specified.

As used herein, the term "or" can be conjunctive or disjunctive.

As used herein, the term "substantially" means to a great or significant extent, but not completely.

As used herein, the term "about" or "approximately" as applied to one or more values of interest, refers to a value that is similar to a stated reference value, or within an acceptable error range for the particular value as determined by one of ordinary skill in the art, which will depend in part on how the value is measured or determined, such as the limitations of the measurement system. In one aspect, the term "about" refers to any values, including both integers and fractional components that are within a variation of up to ±10% of the value modified by the term "about." Alternatively, "about" can mean within 3 or more standard deviations, per the practice in the art. Alternatively, such as with respect to biological systems or processes, the term "about" can mean within an order of magnitude, in some embodiments within 5-fold, and in some embodiments within 2-fold, of a value. As used herein, the symbol "~" means "about" or "approximately."

All ranges disclosed herein include both end points as discrete values as well as all integers and fractions specified within the range. For example, a range of 0.1-2.0 includes 0.1, 0.2, 0.3, 0.4 . . . 2.0. If the end points are modified by the term "about," the range specified is expanded by a variation of up to ±10% of any value within the range or within 3 or more standard deviations, including the end points.

As used herein, the terms "active ingredient" or "active pharmaceutical ingredient" refer to a pharmaceutical agent, active ingredient, compound, or substance, compositions, or mixtures thereof, that provide a pharmacological, often beneficial, effect.

As used herein, the terms "control," or "reference" are used herein interchangeably. A "reference" or "control" level may be a predetermined value or range, which is employed as a baseline or benchmark against which to assess a measured result. "Control" also refers to control experiments or control cells.

As used herein, the term "dose" denotes any form of an active ingredient formulation or composition, including cells, that contains an amount sufficient to initiate or produce a therapeutic effect with at least one or more administrations. "Formulation" and "composition" are used interchangeably herein.

As used herein, the term "prophylaxis" refers to preventing or reducing the progression of a disorder, either to a statistically significant degree or to a degree detectable by a person of ordinary skill in the art.

As used herein, the terms "effective amount" or "therapeutically effective amount," refers to a substantially nontoxic, but sufficient amount of an agent, composition, or cell(s) being administered to a subject that will prevent, treat, or ameliorate to some extent one or more of the symptoms of the disease or condition being experienced or that the subject is susceptible to contracting. The result can be the reduction or alleviation of the signs, symptoms, or causes of a disease, or any other desired alteration of a biological system. An effective amount may be based on factors individual to each subject, including, but not limited to, the subject's age, size, type or extent of disease, stage of the disease, route of administration, the type or extent of supplemental therapy used, ongoing disease process, and type of treatment desired.

As used herein, the term "subject" refers to an animal. Typically, the subject is a mammal. A subject also refers to primates (e.g., humans, male or female; infant, adolescent, or adult), non-human primates, rats, mice, rabbits, pigs, cows, sheep, goats, horses, dogs, cats, fish, birds, and the like. In one embodiment, the subject is a primate. In one embodiment, the subject is a human.

As used herein, a subject is "in need of treatment" if such subject would benefit biologically, medically, or in quality of life from such treatment. A subject in need of treatment does not necessarily present symptoms, particular in the case of preventative or prophylaxis treatments.

As used herein, the terms "inhibit," "inhibition," or "inhibiting" refer to the reduction or suppression of a given biological process, condition, symptom, disorder, or disease, or a significant decrease in the baseline activity of a biological activity or process.

As used herein, "treatment" or "treating" refers to prophylaxis of, preventing, suppressing, repressing, reversing, alleviating, ameliorating, or inhibiting the progress of biological process including a disorder or disease, or completely eliminating a disease. A treatment may be either performed in an acute or chronic way. The term "treatment" also refers to reducing the severity of a disease or symptoms associated with such disease prior to affliction with the disease. "Repressing" or "ameliorating" a disease, disorder, or the symptoms thereof involves administering a cell, composition, or compound described herein to a subject after clinical appearance of such disease, disorder, or its symptoms. "Prophylaxis of" or "preventing" a disease, disorder, or the symptoms thereof involves administering a cell, composition, or compound described herein to a subject prior to onset of the disease, disorder, or the symptoms thereof. "Suppressing" a disease or disorder involves administering a cell, composition, or compound described herein to a subject after induction of the disease or disorder thereof but before its clinical appearance or symptoms thereof have manifest.

As used herein, all percentages (%) refer to mass (or weight, w/w) percent unless noted otherwise.

Described herein are dermatological compositions containing probiotic components and dormant genetically modified organisms that can ameliorate the harmful effects of pathogenic bacteria and augmenting the skin's natural microbiome. The genetically modified C. acnes bacteria are symbiotic on human skin and can provide cosmetic and therapeutic advantages by: modulating oil production to even skin tone; secreting antioxidants; reducing the oxidative stress that leads to accelerated aging; and calming the skin to promote even texture and reduced pore size. The modified C. acnes organisms are designed to traverse the epidermis into the dermis. In the dermis, they consume oil produced from the sebaceous glands, while also releasing antioxidants and anti-inflammatory mediators to prevent the growth and reduce the harmful effects of pathogenic bacteria. This process ultimately allows beneficial bacteria to flourish, helping the skin heal. The compositions described herein combat acne by symbiotically augmenting the skin's natural microbiome.

One embodiment described herein is a dermatological composition comprising one or more growth-arrested genetically modified bacteria or probiotic components; and one or more dermatologically acceptable excipients. In one embodiment, the formulation contains a growth-arrested genetically modified bacteria (e.g., C. acnes) in an anhydrous or substantially anhydrous composition. The lack of water in the composition is necessary to maintain the bacteria in a dormant state. The bacteria remain dormant until the product is applied to the skin where upon the encounter moisture and become revitalized. The bacteria are stable in the formulations for at least 6 months and potentially up to 2 years.

Figure 1:
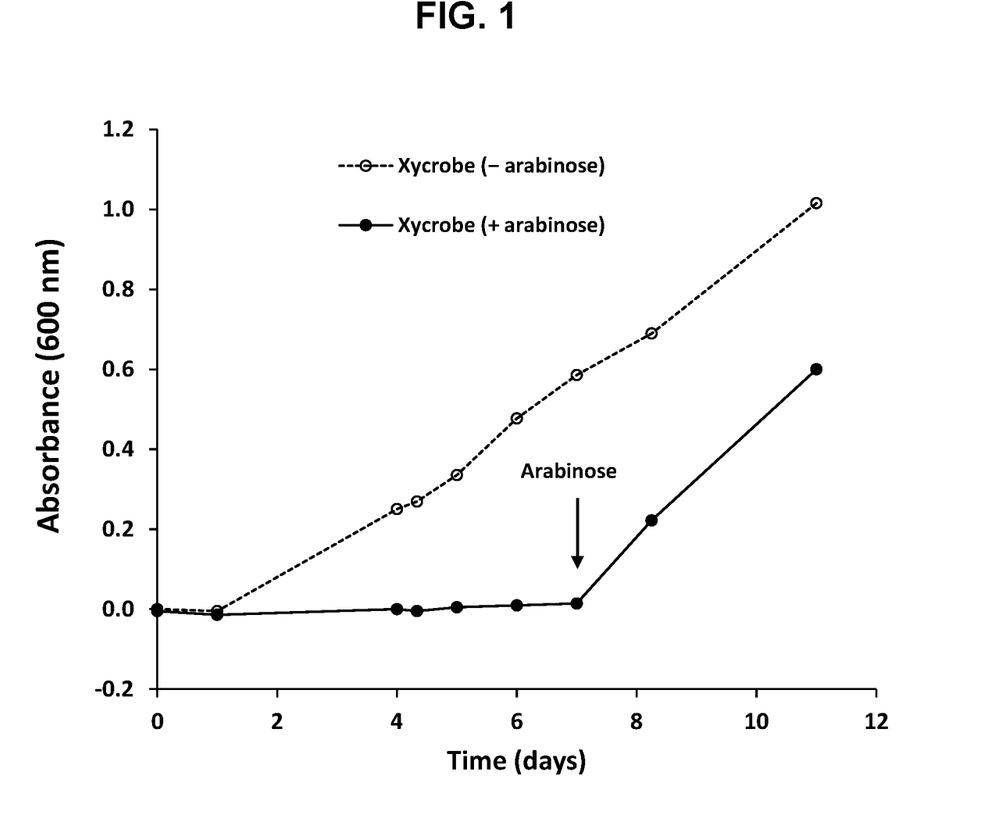
FIG. 1 shows the growth of Xycrobe cells (*C. acnes* RT6 with growth arrested modifications) is dependent upon on the presence of L-(+)-arabinose. Xycrobe cells do not grow in the medium without L-(+)-arabinose, but growth is initiated when arabinose is added.
Figure 2:
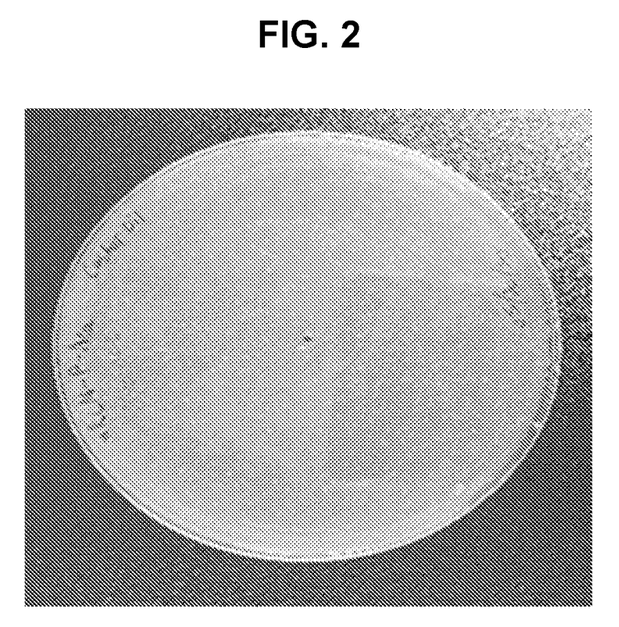
FIG. 2 shows Xycrobe cells (*C. acnes* RT6 with growth arrested modifications) are not inhibited by castor oil. Xycrobe cells were grown in a liquid culture and spread on the plate. Castor oil was then the added to the area with a dot on the plate to check for zone of inhibition. No growth was inhibited.

The compositions described herein containing growth-arrested genetically modified bacteria surprisingly contain a number of components that were previously thought to be bactericidal or detrimental to bacteria. For example, some of the compositions contain castor oil, Vitamin A, or Vitamin A analogues. These compounds were believed to be pernicious to bacteria. See e.g., Al-Mamun et al., BMC Comp. Alt. Med. 16:211 (2016); Momoh et al., Bul. Envir. Pharm. Life Sci. 1: 21-27 (2012); Rampadarath and Puchoo, Asian Pac. J. Trop. Biomedicine 6(2): 100-107 (2016). Thus, it was surprising and unexpected that the C. acnes organisms remained viable in the formulations in the presence of these potentially bactericidal compounds. See FIG. 2. Without being bound by any theory, it is thought that because the bacteria are in a dormant state in the formulation, they are resistant to any effects from the potentially bactericidal compounds in the formulation.

In one aspect, the composition comprises the formulation shown in Table 1.

TABLE 1

Exemplary Composition

| Component | Example | Mass Percentage (%) |
|---|---|---|
| Probiotic Component | Cutibacterium or fermentation medium thereof | ~0.1-5 |
| Dermatologically acceptable excipients | Emollients, gelling agents, vitamins, vitamin analogues, moisturizers, humectants, rheology modifiers, pH modifiers, preservatives, solvents | ~95-99.9 |

In another aspect, the composition comprises the formulation shown in Table 2.

TABLE 2

Exemplary Composition

| Component | Example | Mass Percentage (%) |
|---|---|---|
| Dormant probiotic bacteria | Powdered growth arrested C. acnes | ~0.1-5 |
| Emollient | ethyl olivate, Olea europaea leaf extract, castor oil | ~70-90 |
| Gelling agent | Polyamide-3 (dilinoleic acid, ethylenediamine, polypropylene glycol diamine end-capped with PEG/PPG-32/10 aminopropyl methyl ether) | ~1-15 |

In another aspect, the composition comprises the formulation shown in Table 3.

TABLE 3

Exemplary Composition

| Component | Example | Mass Percentage (%) |
|---|---|---|
| Dormant probiotic bacteria | Powdered growth arrested C. acnes | ~0.1-5 |
| Vitamins or Vitamin analogues | Vitamin A, Vitamin E, Bakuchiol | ~0.1-5 |
| Emollient | ethyl olivate, Olea europaea leaf extract, castor oil | ~70-90 |
| Gelling agent | Polyamide-3 (dilinoleic acid, ethylenediamine, polypropylene glycol diamine end-capped with PEG/PPG-32/10 aminopropyl methy ether) | ~1-15 |

In another aspect, the composition comprises the formulation shown in Table 4.

TABLE 4

Exemplary Composition

| Component | Example | Mass Percentage (%) |
| --- | --- | --- |
| Probiotic antioxidant fermentation product | Fermentation medium from *C. acnes* | ~0.1-5 |
| Vitamins or Vitamin analogues | Vitamin A, Vitamin E, Bakuchiol | ~0.1-5 |
| Moisturizers | Sodium Hyaluronate | ~0.1-5 |
| Humectants | Acetamidoethoxyethanol, sodium protocatechuic acid, sodium lactate, arginine, aspartic acid, protocatechuic acid, glycine, alanine, serine, valine, proline, threonine, isoleucine, histidine, phenylalanine (Prodewe 500) | ~0.1-20 |
| Rheology modifiers | Polyacrylate crosspolymers | ~0.1-5 |
| Film formers | Polyurethane | ~1-5 |
| pH modifiers | Citric acid, other organic acids | ~0.1-5 |
| Preservatives | Benzyl alcohol, sodium benzoate | ~0.1-7 |
| Solvent | Water, deionized water, Rose water, hydroessential rose (*Rosa damascena*) | ~50-95 |

Dermatologically acceptable excipients useful for the compositions as described herein can further comprise any of the following or combinations thereof: acidifying agents (acetic acid, glacial acetic acid, citric acid, fumaric acid, hydrochloric acid, diluted hydrochloric acid, malic acid, nitric acid, phosphoric acid, diluted phosphoric acid, sulfuric acid, tartaric acid); alkalizing agents (ammonia solution, ammonium carbonate, diethanolamine, diisopropanolamine, potassium hydroxide, sodium bicarbonate, sodium borate, sodium carbonate, sodium hydroxide, trolamine); antifoaming agents (dimethicone, simethicone); antimicrobial preservatives (benzalkonium chloride, benzalkonium chloride solution, benzethonium chloride, benzoic acid, benzyl alcohol, butylparaben, cetylpyridinium chloride, chlorobutanol, chlorocresol, cresol, dehydroacetic acid, ethylparaben, methylparaben, methylparaben sodium, phenol, phenylethyl alcohol, phenylmercuric acetate, phenylmercuric nitrate, potassium benzoate, potassium sorbate, propylparaben, propylparaben sodium, sodium benzoate, sodium dehydroacetate, sodium propionate, ascorbic acid, thimerosal, thymol); antioxidants (ascorbic acid, ascorbyl palmitate, butylated hydroxyanisole, butylated hydroxytoluene, hypophosphorous acid, monothioglycerol, propyl gallate, sodium formaldehyde sulfoxylate, sodium metabisulfite, sodium thiosulfate, sulfur dioxide, tocopherol, tocopherols excipient); buffering agents (acetic acid, ammonium carbonate, ammonium phosphate, boric acid, citric acid, lactic acid, phosphoric acid, potassium citrate, potassium metaphosphate, potassium phosphate monobasic, sodium acetate, sodium citrate, sodium lactate solution, dibasic sodium phosphate, monobasic sodium phosphate, phosphate buffer saline); chelating agents (edetate disodium, ethylenediaminetetraacetic acid and salts, edetic acid); coating agents (sodium carboxymethylcellulose, cellulose acetate, cellulose acetate phthalate, ethylcellulose, gelatin, pharmaceutical glaze, hydroxypropyl cellulose, hydroxypropyl methylcellulose, hydroxypropyl methylcellulose phthalate, methacrylic acid copolymer, methylcellulose, polyvinyl acetate phthalate, shellac, sucrose, titanium dioxide, carnauba wax, microcrystalline wax, zein); colorants (caramel, red, yellow, black or blends, ferric oxide); complexing agents (ethylenediaminetetraacetic acid and salts (EDTA), edetic acid, gentisic acid ethanolamide, oxyquinoline sulfate); desiccants (calcium chloride, calcium sulfate, silicon dioxide); emulsifying and/or solubilizing agents (acacia, cholesterol, diethanolamine (adjunct), glyceryl monostearate, lanolin alcohols, mono- and di-glycerides, monoethanolamine (adjunct), lecithin, oleic acid (adjunct), oleyl alcohol (stabilizer), poloxamer, polyoxyethylene 50 stearate, polyoxyl 35 castor oil, polyoxyl 40 hydrogenated castor oil, polyoxyl 10 oleyl ether, polyoxyl 20 cetostearyl ether, polyoxyl 40 stearate, polysorbate 20, polysorbate 40, polysorbate 60, polysorbate 80, diacetate, monostearate, sodium lauryl sulfate, sodium stearate, sorbitan monolaurate, sorbitan monooleate, sorbitan monopalmitate, sorbitan monostearate, stearic acid, trolamine, emulsifying wax); filtering aids (powdered cellulose, purified siliceous earth); flavors and perfumes (anethole, benzaldehyde, ethyl vanillin, menthol, methyl salicylate, monosodium glutamate, orange flower oil, peppermint, peppermint oil, peppermint spirit, rose oil, rose water, thymol, tolu balsam tincture, vanilla, vanilla tincture, vanillin); humectants (glycerol, hexylene glycol, sorbitol); plasticizers (e.g., castor oil, diacetylated monoglycerides, diethyl phthalate, glycerol, mono- and di-acetylated monoglycerides, propylene glycol, triacetin, triethyl citrate); polymers (e.g., cellulose acetate, alkyl celluloses, hydroxyalkyl, acrylic polymers and copolymers); solvents (acetone, alcohol, diluted alcohol, amylene hydrate, benzyl benzoate, butyl alcohol, carbon tetrachloride, chloroform, corn oil, cottonseed oil, ethyl acetate, glycerol, hexylene glycol, isopropyl alcohol, methyl alcohol, methylene chloride, methyl isobutyl ketone, mineral oil, peanut oil, propylene carbonate, sesame oil, water for injection, sterile water for injection, sterile water for irrigation, purified water); sorbents (powdered cellulose, charcoal, purified siliceous earth); carbon dioxide sorbents (barium hydroxide lime, soda lime); stiffening agents (hydrogenated castor oil, cetostearyl alcohol, cetyl alcohol, cetyl esters wax, hard fat, paraffin, polyethylene excipient, stearyl alcohol, emulsifying wax, white wax, yellow wax); suspending and/or viscosity-increasing agents (acacia, agar, alginic acid, aluminum monostearate, bentonite, purified bentonite, magma bentonite, carbomer, carboxymethylcellulose calcium, carboxymethylcellulose sodium, carboxymethylcellulose sodium carrageenan, microcrystalline and carboxymethylcellulose sodium cellulose, dextrin, gelatin, guar gum, hydroxyethyl cellulose, hydroxypropyl cellulose, hydroxypropyl methylcellulose, magnesium aluminum silicate, methylcellulose, pectin, polyethylene oxide, polyvinyl alcohol, povidone, alginate, silicon dioxide, colloidal silicon dioxide, sodium alginate, tragacanth, xanthan gum); sweetening agents (aspartame, dextrates, dextrose, excipient dextrose, fructose, mannitol, saccharin, calcium saccharin, sodium saccharin, sorbitol, solution sorbitol, sucrose, compressible sugar, confectioner's sugar, syrup); surfactants (simethicone); binders (acacia, alginic acid, sodium carboxymethylcellulose, microcrystalline cellulose, dextrin, ethylcellulose, gelatin, liquid glucose, guar gum, hydroxypropyl methylcellulose, methylcellulose, polyethylene oxide, povidone, pregelatinized starch, syrup); diluents (calcium carbonate, dibasic calcium phosphate, tribasic calcium phosphate, calcium sulfate, microcrystalline cellulose, powdered cellulose, dextrates, dextrin, dextrose excipient, fructose, kaolin, lactose, mannitol, sorbitol, starch, pregelatinized starch, sucrose, compressible sugar, confectioner's sugar); disintegrants (alginic acid, microcrystalline cellulose, croscarmellose sodium, crospovidone, polacrilin potassium, sodium starch glycolate, starch, pregelatinized starch); lubricants (calcium stearate, glyceryl behenate, magnesium stearate, light mineral oil, sodium stearyl fumarate, stearic acid, purified stearic acid, talc, hydrogenated vegetable oil, zinc stearate); thickening agents (gelatin having a bloom strength of 50-100); tonicity agent (dextrose, glycerol, mannitol, potassium chloride, sodium chloride); vehicle: flavored and/or sweetened (aromatic elixir, compound benzaldehyde elixir, iso-alcoholic elixir, peppermint water, sorbitol solution, syrup, tolu balsam syrup); vehicle: oleaginous (almond oil, corn oil, cottonseed oil, ethyl oleate, isopropyl myristate, isopropyl palmitate, mineral oil, light mineral oil, myristyl alcohol, octyl dodecanol, olive oil, peanut oil, persic oil, sesame oil, soybean oil, squalane); vehicle: solid carrier (sugar spheres); vehicle: sterile (bacteriostatic water for injection, bacteriostatic sodium chloride injection); viscosity-increasing (see suspending agent); water repelling agents (cyclomethicone, dimethicone, simethicone); and/or solubilizing agent (benzalkonium chloride, benzethonium chloride, cetylpyridinium chloride, docusate sodium, nonoxynol 9, nonoxynol 10, octoxynol 9, poloxamer, polyoxyl 35 castor oil, polyoxyl 40, hydrogenated castor oil, polyoxyl 50 stearate, polyoxyl 10 oleyl ether, polyoxyl 20, cetostearyl ether, polyoxyl 40 stearate, polysorbate 20, polysorbate 40, polysorbate 60, polysorbate 80, sodium lauryl sulfate, sorbitan monolaurate, sorbitan monooleate, sorbitan monopalmitate, sorbitan monostearate, tyloxapol). This list is not meant to be exclusive, but instead merely representative of the classes of excipients and the particular excipients that may be used in the formulations described herein. See *Remington's Essentials of Pharmaceutics*, Pharmaceutical Press Publishing Company, London, UK, 1$^{st}$ Edition, 2013, and the *Handbook of Pharmaceutical Excipients*, 8$^{th}$ Edition, Pharmaceutical Press Publishing Company London, U K, 2017, each of which is incorporated by reference herein for such teachings.

Another embodiment described herein is an anhydrous dermatological composition comprising: about 0.1% to about 5% by mass of one or more wild type or growth-arrested genetically modified bacteria or probiotic components; and about 95% to about 99.9% by mass of one or more dermatologically acceptable anhydrous excipients. In one aspect, the dermatologically acceptable anhydrous excipients comprise one or more emollients, humectants, moisturizers, vitamins, vitamin analogues, gelling agents, rheology modifiers, pH modifiers, or preservatives; and optionally, one or more solvents.

Another embodiment described herein is an anhydrous dermatological composition comprising: one or more wild type or growth-arrested genetically modified microorganisms; and one or more dermatologically acceptable anhydrous excipients comprising one or more emollients, humectants, vitamins, vitamin analogues, or gelling agents. In one aspect, the anhydrous dermatological composition maintains the growth-arrested genetically modified microorganisms in a dormant state for at least six months and up to about 2 years.

In one embodiment, the microorganism can comprise organisms of the genus *Cutibacterium*. In another embodiment, the microorganism comprises a species selected from *Cutibacterium acidifaciens, Cutibacterium acidipropionici, Cutibacterium acnes, Cutibacterium australiense, Cutibacterium avidum, Cutibacterium cyclohexanicum, Cutibacterium freudenreichii, Cutibacterium granulosum, Cutibacterium jensenii, Cutibacterium microaerophilum, Cutibacterium propionicum*, or *Cutibacterium thoenii*. In one embodiment the microorganism is *Cutibacterium acnes*. In one embodiment, the *Cutibacterium acnes* comprises a CRISPR (clustered regularly interspaced short palindromic repeat) array. In one embodiment, the microorganism is *C. acnes*, type II, ribotype 6 (e.g., *C. acnes* RT6). In another embodiment the microorganism is *C. acnes* roxP.

Another embodiment described herein is an anhydrous dermatological composition comprising: about 0.1% to about 5% by mass of a growth-arrested strain of *C. acnes*; and about 95% to about 99.9% by mass of one or more dermatologically acceptable anhydrous excipients comprising one or more emollients, humectants, vitamins, vitamin analogues, or gelling agents. In one aspect, the anhydrous dermatological composition maintains the growth-arrested strain of *C. acnes* in a dormant state for at least six months and up to about 2 years. In another aspect, the composition comprises: about 1% to 2% by mass of the growth-arrested strain of *C. acnes*; about 90% by mass of one or more emollients; and about 10% by mass of one or more gelling agents. In another aspect, the growth-arrested strain of *C. acnes* comprises a lyophilized powder comprising *C. acnes*, sodium chloride, calcium stearate, and inulin (fructose polysaccharide). In another aspect, the emollients comprise ethyl olivate, *Olea europaea* leaf extract, and castor oil; and the gelling agent comprises Polyamide-3 (dilinoleic acid, ethylenediamine, polypropylene glycol diamine end-capped with PEG/PPG-32/10 aminopropyl methyl ether). In another aspect, the composition comprises: about 0.1-5% by mass of the growth-arrested strain of *C. acnes*; about 55-95% by mass of ethyl olivate and *Olea europaea* leaf extract; about 20-40% by mass of castor oil; and about 1-15% by mass of Polyamide-3 (dilinoleic acid, ethylenediamine, polypropylene glycol diamine end-capped with PEG/PPG-32/10 aminopropyl methyl ether). In another aspect, the composition comprises: about 1% to 2% by mass of a growth-arrested strain of *C. acnes*; about 1% by mass of Vitamin A or a vitamin A analogue; about 90% by mass of one or more emollients; and about 10% by mass of one or more gelling agents. In another aspect, the composition comprises: about 0.1-5% by mass of the growth-arrested strain of *C. acnes*; about 0.1-5% by mass of retinol; about 0.1-5% by mass of Vitamin A palmitate; about 50-75% by mass of ethyl olivate and *Olea europaea* leaf extract; about 20-40% by mass of castor oil; and about 1-15% by mass of Polyamide-3 (dilinoleic acid, ethylenediamine, polypropylene glycol diamine end-capped with PEG/PPG-32/10 aminopropyl methyl ether).

Another embodiment described herein is an aqueous dermatological composition comprising: about 0.1% to about 5% by mass of probiotic composition; and about 95% to about 99.9% by mass of one or more dermatologically acceptable excipients comprising one or more humectants, moisturizers, rheology modifiers, pH modifiers, preservatives, or solvents. In one aspect, the probiotic composition comprises a *C. acnes* fermentation product comprising lyophilized powder of purified *C. acnes* roxP fermentation media. In another aspect, the *C. acnes* fermentation product is purified using filtration and diafiltration. In another aspect, the composition comprises: about 0.1% to 5% by mass of the *C. acnes* fermentation product; about 80% by mass of one or more solvents; about 10% by mass of one or more humectants; about 1% by mass of one or more moisturizers; about 2% by mass of one or more rheology modifiers; about 4% by mass of one or more film formers; about 2% by mass of one or more preservatives; and about 1% by mass of one or more pH modifiers. In another aspect, the composition comprises: about 0.1-5% by mass of the *C. acnes* fermentation product; about 70-90% by mass of water; about 0.1-5% by mass of sodium hyaluronate solution; about 5-15% by mass of acetamidoethoxyethanol; about 1-5% by mass of polyurethane; about 0.1-5% by mass of a solution of sodium protocatechuic acid, sodium lactate, protocatechuic acid, arginine, aspartic acid, glycine, alanine, serine, valine, proline, threonine, isoleucine, histidine, and phenylalanine (Prodew® 500); about 0.1-5% by mass of hydroxyethyl acrylate, sodium acryloyldimethyl taurate copolymer; about 0.1-5% by mass of polyacrylate crosspolymer-6; about 0.1-5% by mass of benzyl alcohol; about 0.5-1.5% by mass of sodium benzoate and potassium sorbate; and about 0.1-5% by mass of citric acid solution (50%). In another aspect, the composition further comprises about 0.1% to about 2% by mass retinoid.

Another embodiment described herein is a method for manufacturing the compositions described herein. In one aspect, the method comprising combining the ingredients of the composition. The ingredients may be combined in any order or in specific phases. For example, components of one phase may be combined, and components of any other phase(s) may be combined and then the two separate phases combined and mixed to homogeneity. Heating and mixing may be used individually or in combination to facilitate homogenization.

Another embodiment described herein is a cosmetic or therapeutic composition prepared by any of the methods or means described herein.

Another embodiment described herein is a method for preparing a probiotic fermentation product, the method comprising: growing a microorganism in a fermentation medium; separating the fermentation medium from the organism; performing tangential flow filtration on the fermentation media with buffer exchanges to remove small molecule contaminants to produce a purified fermentation product; and lyophilizing the purified fermentation product. In one aspect, the microorganism is *C. acnes* roxP.

Another embodiment described herein is a fermentation product produced by the any of the methods or means described herein.

It will be apparent to one of ordinary skill in the relevant art that suitable modifications and adaptations to the compositions, formulations, methods, processes, and applications described herein can be made without departing from the scope of any embodiments or aspects thereof. The compositions and methods provided are exemplary and are not intended to limit the scope of any of the specified embodiments. All the various embodiments, aspects, and options disclosed herein can be combined in any variations or iterations. The scope of the compositions, formulations, methods, and processes described herein include all actual or potential combinations of embodiments, aspects, options, examples, and preferences herein described. The compositions, formulations, or methods described herein may omit any component or step, substitute any component or step disclosed herein, or include any component or step disclosed elsewhere herein. The ratios of the mass of any component of any of the compositions or formulations disclosed herein to the mass of any other component in the formulation or to the total mass of the other components in the formulation are hereby disclosed as if they were expressly disclosed. Should the meaning of any terms in any of the patents or publications incorporated by reference conflict with the meaning of the terms used in this disclosure, the meanings of the terms or phrases in this disclosure are controlling. Furthermore, the specification discloses and describes merely exemplary embodiments. All patents and publications cited herein are incorporated by reference herein for the specific teachings thereof.

EXAMPLES

Example 1

The formula for the Xycrobe Live Probiotic Gel is made up of four (4) ingredients including the live bacteria strain of *Cutibacterium acnes* (*Propionibacterium acnes*) that has been genetically modified to be growth arrested. The formulation is shown in Table 5.

TABLE 5

| | | | | |
|---|---|---|---|---|
| | | Live Probiotic Gel | | |
| Phase | Component | Function | Percent Mass (%) | Percent Mass Range (%) |
| A | Xycrobe Powder | Probiotic | 1.1 | ~0.5-3 |
| A | Ethyl olivate and *Olea europaea* leaf extract (Sensolene ® Light ET) | Emollient | 5.0 | ~5-20 |
| B | Ethyl olivate and *Olea europaea* leaf extract (Sensolene ® Light ET) | Emollient | 60.9 | ~50-75 |
| B | Castor Oil (Seatons Virgin Castor Oil) | Emollient | 25.0 | ~20-40 |
| B | Polyamide-3 (OleoCraft ™ MP-30) | Gelling Agent | 8.0 | ~1-15 |
| | | Sum | 100% | 100% |

The formulation is prepared as follows:
1. Phase "B" is added together and heated to 90-100° C. with stirring;
2. While Phase "B" is heating, Xycrobe Powder is dispersed into ethyl olivate and *Olea europaea* leaf extract (Sensolene® Light ET) through high sheer mixing to make Phase "A;"
3. After all solids are dissolved in Phase "B" the solution is cooled until solid;
4. Phase "A" is incorporated into Phase "B" with mixing.

The Live Probiotic Gel formula disclosed in Table 5 is the vehicle chosen to deliver the Xycrobe strain of *Cutibacterium acnes* (formerly *Propionibacterium acnes*) to the skin. The vehicle is an anhydrous gel with shear thinning properties. An anhydrous formula was required to extend the shelf life of the product by preventing the Xycrobes from multiplying in the base due to the absence of water. The polyamide-3 structuring agent (20,000 Da) traps the emollient oils in the formula through hydrophobic pockets while the polymers are locked to each other through hydrogen bonding. Thus, the product maintains a viscous gel structure with the freeze dried Xycrobes suspended. Once enough shear has been imparted onto the vehicle the structuring agent breaks down releasing the emollient oils allowing the formula to be spread across the skin. The polyamide-3 structuring agent has a secondary benefit of creating a water-resistant film on the skin, which helps keep the skin hydrated and allows the freeze dried Xycrobes to propagate. Sensolene® Light ET was chosen as the primary emollient for the base as it provides a light and dry feel on the skin. Castor oil was chosen as a secondary emollient for two purposes. First, it is non-drying to the skin and second, because it is a triester of ricinoleic acid and glycerol, which contains several hydroxyls (—OH) functional groups, it aids in the formation of the gel.

The finished product was screened for viability of the Xycrobe strain via serial dilution of the gel onto a modified RCM-potato peptone, arabinose media. This screening process checks for the total colony forming units (CFUs) of Xycrobes in the finished product corresponding to a single daily dose. An RT-PCR assay was performed on the Xycrobes prior to lyophilization to ensure the purity of the Xycrobe raw material strain. The lyophilization process of the Xycrobe powder creates a stable raw material allowing for easier incorporation into the anhydrous gel. The Xycrobe powder is a mixture of Xycrobe cells, sodium chloride, calcium stearate and inulin (fructose polysaccharide).

Example 2

A secondary formula for the Xycrobe Live Probiotic Gel has been developed with the addition of retinoids. The Xycrobe Live Probiotic Gel containing retinoids is prepared similarly to the Xycrobe Live Probiotic Gel Version described above. The formulation is shown in Table 6.

TABLE 6

Live Probiotic Gel with Retinoids

| Phase | Component | Function | Percent Mass (%) | Percent Mass Range (%) |
|---|---|---|---|---|
| A | Xycrobe Powder | Probiotic | 1.1 | ~0.5-3 |
| A | Retinol and *Glycine soya* oil (Retinol 10 SU) Retinyl palmitate and | Retinoid | 1.0 | ~0.1-5 |

TABLE 6-continued

Live Probiotic Gel with Retinoids

| Phase | Component | Function | Percent Mass (%) | Percent Mass Range (%) |
|---|---|---|---|---|
| A | Tocopherol (Vitamin A-Palmitate Care 1.7 9) | Retinoid | 0.36 | ~0.1-5 |
| A | Ethyl olivate and *Olea europaea* leaf extract (Sensolene® Light ET) | Emollient | 3.64 | ~5-20 |
| B | Ethyl olivate and *Olea europaea* leaf extract (Sensolene® Light ET) | Emollient | 60.90 | ~50-75 |
| B | Castor Oil (Seatons Virgin Castor Oil) | Emollient | 25.0 | ~20-40 |
| B | Polyamide-3 (OleoCraft™ MP-30) | Gelling Agent | 8.0 | ~1-15 |
| | | Sum | 100% | 100% |

The preparation of the Xycrobe Live Probiotic Gel containing Retinoids is similar to Xycrobe Live Probiotic Gel described above.

A drawback of the Polyamide-3 (OleoCraft™ MP-30; e.g., dilinoleic acid, ethylenediamine, polypropylene glycol diamine end-capped with PEG/PPG-32/10 aminopropyl methyl ether) structuring agents is the difficulty in gelling silicone systems. See OleoCraft™ Polymers Product Specification, Croda Europe Ltd (January 2017). While silicones provide an optimal sensorial experience, achieving a stable, transparent, and globally approved formula was challenging. The solution to this problem was the incorporation of the emollients, ethyl olivate and *Olea europaea* leaf extract (Sensolene® Light ET). Sensolene® Light ET is a natural origin, globally compliant silicone alternative. In addition to providing the desired sensorial properties, Sensolene® Light ET displays enhanced skin hydration and antioxidant benefits. See SENSOLENE® Light ET Product Specification, Hallstar Beauty, Mar. 13, 2019.

The second major component of the Xycrobe Live Probiotic Gel is Castor Oil. Castor oil has a long history of being known for its anti-microbial activity against several bacterial species. See e.g., Al-Mamun et al., "Characterization and evaluation of antibacterial and antiproliferative activities of crude protein extracts isolated from the seed of *Ricinus communis* in Bangladesh," *BMC Comp. Alt. Med.* 16:211 (2016); Momoh et al., "Evaluation of the antimicrobial and phytochemical properties of oil from castor seeds (*Ricinus communis* linn)," *Bul. Envir. Pharm. Life Sci.* 1: 21-27 (2012); Rampadarath and Puchoo, "In vitro antimicrobial and larvicidal properties of wild *Ricinus communis* L. in Mauritius," *Asian Pac. J. Trop. Biomedicine* 6(2): 100-107 (2016). Seatons Virgin Castor Oil (Croda Personal Care), neat, was found to be non-inhibitory to the growth of Xycrobe cells despite a preponderance of literature describing the anti-microbial activity of castor oil. See FIG. 2. This result was both surprising and unexpected.

The initial Xycrobe raw material only consisted of inulin and Xycrobes. This mixture was found to be impractical for long term storage or scale up. The hygroscopicity of the Xycrobe powder made the raw material susceptible to subtle humidity changes and had to be used shortly after exposure to atmosphere. To combat the hygroscopicity of the powder, 1% calcium stearate and sodium chloride were added to the mixture prior to freeze drying. Calcium stearate was added as a processing aid (anti-adherent) to prevent the powder from clumping to provide a smooth dry powder. A secondary benefit of using calcium stearate is that it helped remove the grittiness of the Xycrobe raw material.

Example 3

A third formulation, Xycrobe Biome Derived Antioxidant Concentrate, contains purified fermentation media from cultures of Xycrobes (*C. acnes* roxP). During the fermentation process of Xycrobes, a complex mixture of nutrients and cellular metabolites is produced. This fermentation product is separated from the Xycrobe cells by filtration (0.22 μm) to give a sterile fermentation product.

The fermentation medium has a potent odor owing to some of the metabolites. To remove the odor of the medium, the media was sequentially filtered and concentrated using diafiltration methods. The fermentation media was concentrated using a 3 kDa or smaller cut-off cellulose or similar material filter in Tangential Flow Filtration (TFF) system. All filtration steps were performed at 4° C. or 25° C. After preparing a sample that has been concentrated at least 20 times, a diafiltration process modified for this purpose was performed. By exchanging the buffer using PBS, odor-causing small molecular weight components remaining in the concentrate were removed and only substances having antioxidant and anti-inflammatory effects were obtained.

The fermentation product (Xycrobe Biome Derived Antioxidant Concentrate) was stored as a concentrate.

The main constituent of the Xycrobe Biome Derived Antioxidant Concentrate is purified water. The process for preparing the concentrate as described herein removes the odor of the fermentation product. A preservative is used to prevent microbial contamination. Several ingredients were screened to determine a preservative that was efficacious in preventing microbial contamination, but not detrimental to the live Xycrobes that are applied to the skin through the use of the other Xycrobe products recommended for the Xycrobe Regimen. The preservative chosen was benzyl alcohol at 0.1-5%. Benzyl alcohol is highly tolerated on the skin and is effective across a broad pH range. The system was thickened into a gel using a combination of two polymers (polyacrylate crosspolymer-6 (e.g., (Sepimax™ Zen) and hydroxyethyl acrylate/sodium acryloyldimethyl taurate copolymer (e.g., (Sepinov™ EMT 10) at a 1:1 ratio. The formulation is shown in Table 7.

TABLE 7

Xycrobe Biome-Derived Antioxidant Concentrate

| Phase | Component | Function | Percent Mass (%) | Percent Mass Range (%) |
|---|---|---|---|---|
| A | Xycrobe roxP fermentation product | Postbiotic | 3.0 | ~0.1-5 |
| A | Purified water | Solvent | 70.0 | ~50-90 |
| A | Benzyl Alcohol | Preservative | 1.0 | ~0.1-5 |
| A | Sodium Hyaluronate Solution (HyaClear ® Solution) | Moisturizer | 1.0 | ~0.1-5 |
| A | Acetamidoethoxyethanol (ElfaMoist ® AC) | Humectant | 10.0 | ~5-15 |
| A | Sodium protocatechuic acid, sodium lactate, arginine, aspartic acid, protocatechuic acid, glycine, alanine, serine, valine, proline, threonine, isoleucine, histidine, phenylalanine (Prodew ® 500) | Humectant | 1.0 | ~0.1-5 |
| A | Sodium benzoate and potassium sorbate solution (aqueous) (euxyl ® K 712) | Preservative | 1.0 | ~0.5-1.5 |
| A | Polyurethane-35 aqueous (Baycusan ® C 1004) | Film former | 4.0 | ~1-5 |
| B | Citric acid solution (50%) | pH Modifier | q.s. | ~0.1-5 |
| C | Polyacrylate Crosspolymer-6 (Sepimax ™ Zen) | Rheology Modifier | 1.2 | ~0.1-5 |
| C | Hydroxyethyl acrylate, sodium acryloyldimethyl taurate copolymer (Sepinov ™ EMT 10) | Rheology Modifier | 1.2 | ~0.1-5 |
| D | Purified water | Solvent | 6.60 | ~1-10 |
| | Sum | | 100% | 100% |

In another embodiment, the composition shown in Table 7 further comprises a fat-soluble vitamin including Vitamin A (retinol), a Vitamin A analogue (e.g., Vit. A palmitate, bakuchiol), Vitamin E, Vitamin D, or Vitamin K, or analogues thereof. In one aspect, the composition shown in Table 7 further comprises retinol or a retinoid at a mass percentage of about 0.1% to about 2%, including all integers within the range.

The formula for the Xycrobe Biome-Derived Antioxidant Concentrate is shown in Table 7. The formulation is prepared as follows:
1. Phase "A" ingredients are combined with mixing;
2. Phase "B" is added until the pH of the system is 4.5-5.0 to make Phase "AB";
3. Phase "C" ingredients are slowly added to Phase "AB" to make Phase "ABC"; and
4. Phase "D" is added to the "ABC" mixture quantum sufficiat.

Figure 3:
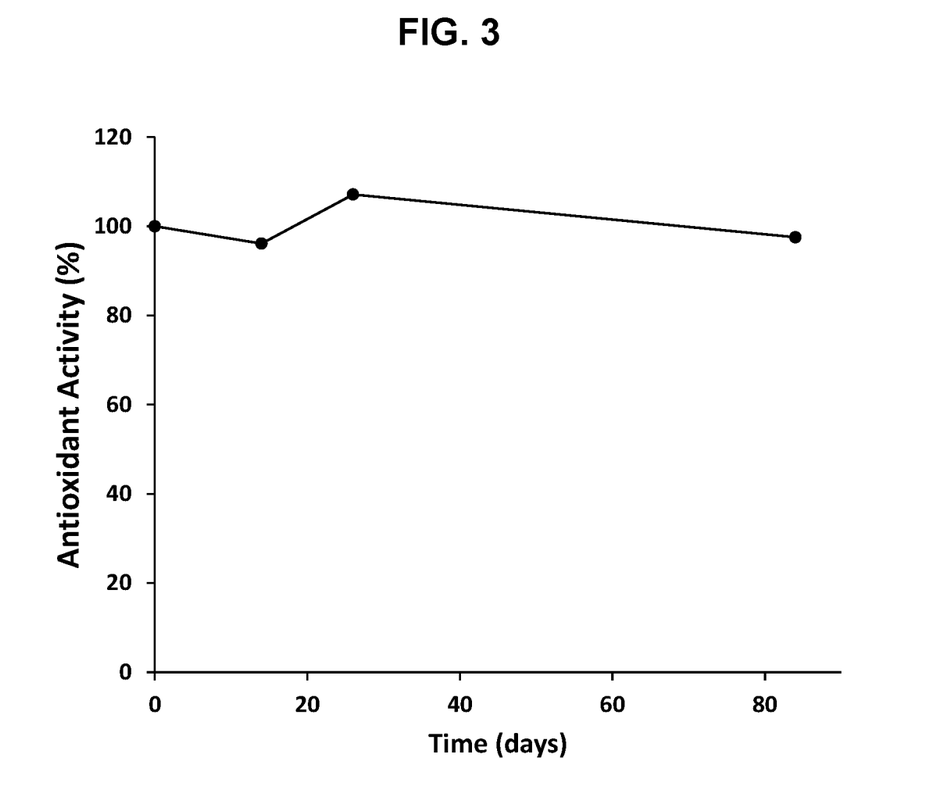
FIG. 3 shows that the antioxidant activity of the Xycrobe (*C. acnes* roxP) fermentation derived antioxidant concentrate is stable over 84 days.

The antioxidant activity of the Xycrobe Biome Derived Antioxidant Concentrate was quantified using the OxiSelect™ Trolox Equivalent Antioxidant Capacity (TEAC) Assay kit. The TEAC assay measures the amount of antioxidant against a Trolox standard. Trolox is an antioxidant (a Vitamin E derivative). The TEAC kit is standardized by adding oxidized ABTS substrate to Trolox and measuring the absorbance of the solution. As the substrate is reduced, the solution clears and the absorbance decreases. The was stored at room temperature and after 14, 26, and 84 days. Samples were obtained, and the antioxidant activity was measured over time. FIG. 3 shows that the antioxidant activity of the concentrate is stable over 84 days.

What is claimed:
1. A dermatological composition consisting of:
an anhydrous formulation of:
about 0.1% to about 5% by mass of a dry growth-arrested genetically modified strain of *Cutibacterium acnes* (*C. acnes*) that remains in a dormant state for at least six months and up to about 2 years;
about 55% to about 95% by mass of one or more anhydrous emollients comprising ethyl olivate or *Olea europaea* leaf extract; and
about 1% to about 15% by mass of one or more anhydrous gelling agents comprising Polyamide-3.

2. A dermatological composition consisting of:
an anhydrous formulation of:
about 0.1% to about 5% by mass of a dry wild-type or growth-arrested genetically modified strain of *Cutibacterium acnes* (*C. acnes*) that remains in a dormant state for at least six months and up to about 2 years;
about 55% to about 95% by mass of one or more anhydrous emollients comprising ethyl olivate or *Olea europaea* leaf extract; and
about 1% to about 15% by mass of one or more anhydrous gelling agents comprising Polyamide-3.

* * * * *